United States Patent [19]

Sherman et al.

[11] 4,456,774
[45] Jun. 26, 1984

[54] BULK SEPARATION OF POLYHYDRIC ALCOHOLS BY SELECTIVE ADSORPTION ON ZEOLITIC MOLECULAR SIEVES

[75] Inventors: John D. Sherman, Chappaqua; Chien C. Chao, Millwood, both of N.Y.

[73] Assignee: Union Carbide Corporation, Danbury, Conn.

[21] Appl. No.: 540,915

[22] Filed: Oct. 13, 1983

Related U.S. Application Data

[63] Continuation of Ser. No. 329,608, Dec. 10, 1981, abandoned.

[51] Int. Cl.$^3$ .................. C07C 29/76; C07C 31/26
[52] U.S. Cl. .................................................. 568/872
[58] Field of Search .................................... 568/872

[56] References Cited

U.S. PATENT DOCUMENTS

| | | | |
|---|---|---|---|
| 2,524,414 | 10/1950 | Wolfrom et al. | 568/872 |
| 3,864,406 | 2/1975 | Melaja et al. | 568/872 |
| 3,944,625 | 3/1976 | Neal | 568/868 |
| 4,069,172 | 1/1978 | Kanaoka et al. | 252/455 Z |
| 4,238,243 | 12/1980 | Tu et al. | 252/455 Z |
| 4,257,885 | 3/1981 | Grose et al. | 252/455 Z |
| 4,298,501 | 11/1981 | Kulprathipanja | 252/455 Z |

OTHER PUBLICATIONS

Samuelson et al., "Acta Chemica Scandinavica", 22(1968), 1252–1258.
J. P. Johnson, "Specialized Sugars for the Food Industry", Noyes Data Corp., Parkridge, New Jersey, 313–323, (1976).

*Primary Examiner*—J. E. Evans
*Attorney, Agent, or Firm*—Gary L. Wamer

[57] ABSTRACT

Mannitol is separated from admixture with galactitol and/or from sorbitol by selective adsorption on cationic forms of zeolite X and zeolite Y.

15 Claims, 5 Drawing Figures

F I G. 5
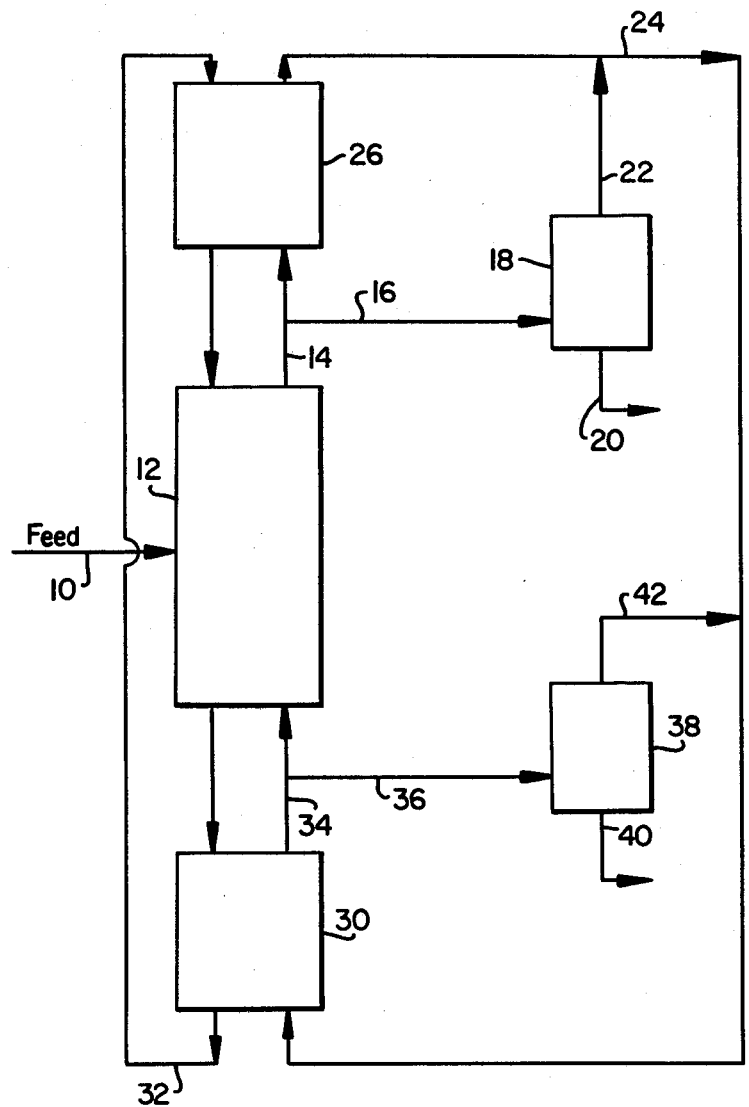

BULK SEPARATION OF POLYHYDRIC ALCOHOLS BY SELECTIVE ADSORPTION ON ZEOLITIC MOLECULAR SIEVES

This is a continuation of application Ser. No. 329,608, filed Dec. 10, 1981 now abandoned.

The present invention relates to the liquid phase separation of mannitol from sorbitol and/or mannitol from galactitol. More particularly, it relates to such a separation by selective adsorption on certain types of zeolite molecular sieves.

Mannitol, sorbitol and galactitol are polyhydric alcohols made by the reduction of sugars. Very often, the reduction reaction products are mixtures of these polyhydric alcohols. Mannitol and sorbitol are especially important commercial polyhydric alcohols in their pure forms.

Mannitol may be produced from invert sugar, fructose or from mannose. In the first instance, sucrose is hydrolyzed to "invert sugar", which is a mixture of glucose and fructose. This mixture is reduced, resulting in a mixture of sorbitol and mannitol in a ratio of approximately 3:1. It is necessary to separate the mannitol from the sorbitol in the mixture in order to obtain a pure product. In general, according to "Specialized Sugars for the Food Industry," by J. P. Johnson, Noyes Data Corporation, Parkridge, N.J. (1976), this is done by successive recrystallizations, an expensive and time-consuming process.

Another method to separate mannitol from sorbitol in admixture is disclosed in U.S. Pat. No. 3,864,406 (Melaja et al.). Melaja et al. teaches the use of the calcium exchanged form of a sulfonated polystyrene cation exchange resin which is crosslinked with divinylbenzene.

Mannitol may also be produced by the hydrogenation of mannose or sources of mannose such as pulping liquors and other hydrolyzates of hemicellulose. Hydrogenation of mannose results in the production of pure mannitol. However, these lignocellulosic sources also contain wood sugars, some of which are hard to separate from mannose. As a result, hydrogenation products of these wood sugars, in particular galactose, must be separated from mannitol in order to obtain a pure product.

Crystallization-type separations of mannitol from galactitol have been disclosed in U.S. Pat. No. 3,944,625 (J. A. Neal). According to that process, the mannitol-galactitol admixture is dissolved in a mixed solvent of alkanol and water, and small amounts of soluble salts of iron, nickel or cobalt are added.

The use of resins in separating sugar alcohols has been found to have several disadvantages compared to the use of zeolite molecular sieves. First, the resins must be used as small beads, and the fine of the resin may be carried through valves and jam them. Also, resins tend to swell when exposed to aqueous solutions. This diminishes the precision of the separations because the volume of resin changes from the beginning to the end of each process run. The zeolite molecular sieves used in this invention do not swell when they encounter water and, therefore, flow rates and volumes can remain uniform throughout the process. Another potential disadvantages to using polystyrene resins is due to their organic nature. It is therefore an object of this invention to provide an efficient process for the separation of sugar alcohols.

It is also an object of this invention to provide a precise process for separating mannitol from galactitol and/or from sorbitol.

It is a further object of this invention to provide a process for separation of sugar alcohols by selective absorption on inorganic zeolite molecular sieves.

It has been discovered that certain zeolites are well-suited to separating mannitol from sorbitol and mannitol from galactitol.

BRIEF DESCRIPTION OF FIGURES

FIG. 5 shows one method in which the process of this application may be employed.

DESCRIPTION OF THE INVENTION

Figure 1:
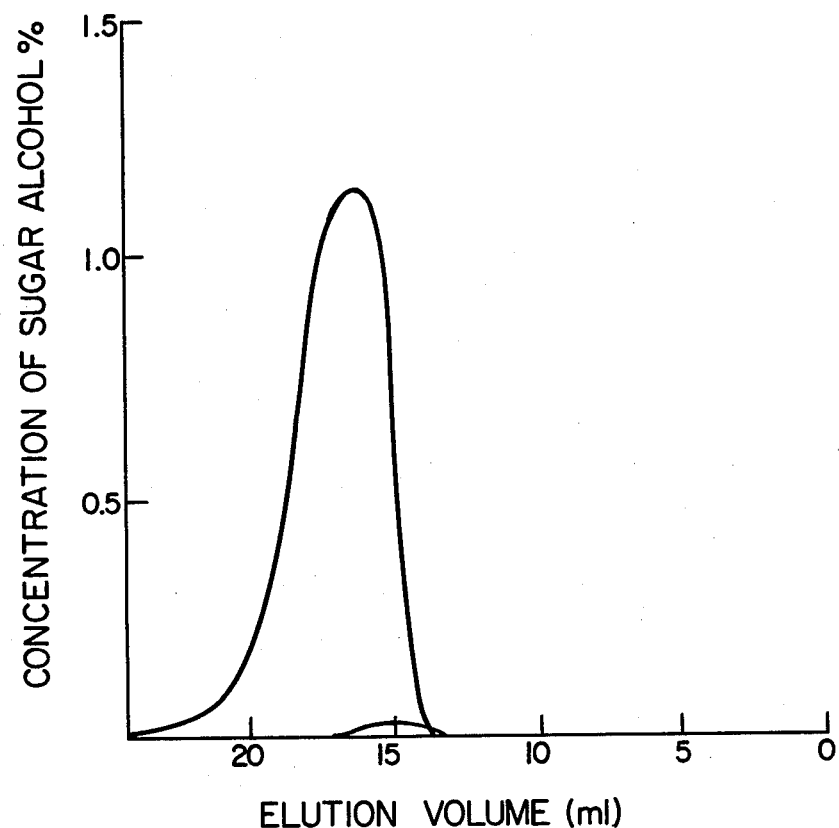
FIGS. 1 and 2 show elution curves of polyhydric alcohols where the separation medium is potassium-substituted zeolite Type Y.

The present invention comprises a process for the separation of mixtures of polyhydric alcohols, said mixtures comprising mannitol and one or more members of the group consisting of sorbitol and galactitol, by selective adsorption which comprises contacting a mixture comprising said compounds at a temperature of from 30° C. to 100° C. and at a pressure sufficient to maintain the system in the liquid phase with an adsorbent composition comprising at least one crystalline aluminosilicate zeolite selected from a group consisting of zeolite type Y and zeolite type X wherein the zeolitic cations which occupy more than 55% the available cation sites are selected from the group consisting of barium and calcium; whereby a polyhydric alcohol is selectively adsorbed theron, removing the non-adsorbed portion of said mixture from contact with the zeolite adsorbent; and desorbing the adsorbate therefrom by contacting said adsorbent with a desorbing agent and recovering the desorbed polyhydric alcohol.

Zeolite Y and the method for its manufacture are described in detail in U.S. Pat. No. 3,130,007, issued Apr. 21, 1964 to D. W. Breck. Zeolite X and the method for its manufacture are described in detail in U.S. Pat. No. 2,882,244, issued Apr. 14, 1959 to R. M. Milton.

The adsorption affinities of various zeolites for sugars was determined by a "pulse test". This test consisted of packing a column with the appropriate zeolite, placing it in a block heater to maintain constant temperature, and eluting solutions through the column with water to determine retention volume of solute. The retention volume of solute is defined as elution volume of solute minus "void volume". "Void volume" is the volume of solvent needed to elute a non-sorbing solute through the column. A soluble polymer of fructose, inulin, which is too large to be sorbed into the zeolite pores, was chosen as the solute to determine void volume. The elution volume of inulin was first determined. The elution volumes of sugars were then determined undersimilar experimental conditions. The retention volumes were calculated and are recorded in Table I, below. From the retention volume data, the separation factors (S.F.), $\dfrac{\text{Mannitol}}{\alpha \text{Galactitol}}$ $(S.F._{\frac{M}{G}})$ and $\dfrac{\text{Sorbitol}}{\alpha \text{Mannitol}}$ $(S.F._{\frac{S}{M}})$, where -continued $\frac{M}{G}$ stands for $\frac{Mannitol}{Galactitol}$ and $\frac{S}{M}$ stands for $\frac{Sorbital}{Mannitol}$ were calculated in accordance with the following equations:

$$S.F._{\frac{M}{G}} = \alpha \text{ (mannitol/galactitol)}$$

$$= \frac{\text{(retention volume for mannitol peak)}}{\text{(retention volume for galactitol peak)}}$$

$$S.F._{\frac{S}{M}} = \alpha \text{ (sorbitol/mannitiol)}$$

$$= \frac{\text{(retention volume for sorbitol peak)}}{\text{(retention volume for mannitol peak)}}$$

A S.F.$_{M/G}$ factor greater than unity indicates that the particular adsorbent was selective for mannitol over galactitol. A S.F.$_{S/M}$ greater than unity indicates that the particular adsorbent was selective for sorbitol over mannitol. The separation factor values calculated according to the above-mentioned method are found in Table II.

In order to show more dramatically the ability to separate sugar alcohols, Table II includes a column showing the difference between the α-value and 1.00 multiplied by one hundred. This clearly indicates each zeolite's ability to perform the desired separations.

TABLE I

| RETENTION VOLUME OF SUGAR ALCOHOLS (in ml) | | | | |
|---|---|---|---|---|
| Column Dimension: | 40 cm × 0.77 cm I.D. | | | |
| Zeolite Form: | Powder except where indicated | | | |
| Flow Rate: | 1 ml/min. | | | |
| Temperature: | 160° F. | | | |
| Zeolite | Inulin | Galactitol | Mannitol | Sorbitol |
| KX | 0 | | 3.0 | 2.8 |
| KY | 0 | 1.4 | 1.3 | 1.2 |
| NaX | 0 | | 2.3 | 2.3 |
| NaY | 0 | 1.5 | 1.7 | 1.8 |
| *LiY | 0 | | 2.5 | 2.5 |
| BaX | 0 | 8.7 | 13.6 | 21.7 |
| *BaY | 0 | 13.0 | 15.0 | 12.3 |
| *SrX | 0 | ~7.2 | 7.2 | 8.0 |
| *SrY | 0 | 11.5 | 12.0 | 11.3 |
| CaX | 0 | ~7 | 6.7 | 6.8 |
| CaY | 0 | 10.1 | 11.6 | 13.1 |

*Zeolite in mesh form.

TABLE II

| SEPARATION FACTORS OF SUGAR ALCOHOL SEPARATIONS | | | | |
|---|---|---|---|---|
| Zeolite | Mannitol $^\alpha$Galactitol | α-1 × 100 | Sorbitol $^\alpha$Mannitol | α-1 × 100 |
| KX | | | 0.93 | 7 |
| KY | ~1.0 | 0 | 0.92 | 8 |
| NaX | | | 1.00 | 0 |
| NaY | 1.13 | 13 | 1.06 | 6 |
| LiY | | | 1.0 | 0 |
| BaX | 1.6 | 60 | 1.6 | 60 |
| BaY | 1.15 | 15 | 0.82 | −18 |
| SrX | 0 | 0 | 1.11 | 11 |
| SrY | 1.04 | 4 | 0.94 | −6 |
| CaX | 1.0 | 0 | 1.01 | 1 |
| CaY | 1.15 | 15 | 1.13 | 13 |

In separating mannitol from galactitol or sorbitol in the present process, a bed of solid zeolite adsorbent is preferentially loaded with adsorbates, the unadsorbed or raffinate mixture is removed from the adsorbent bed, and the adsorbed sugar alcohol is then desorbed from the zeolite adsorbent by a desorbant. The adsorbent can, if desired, be contained in a single bed, a plurality of beds in which conventional swing-bed operation techniques are utilized, or a simulated moving-bed countercurrent type of apparatus. A preferred mode of operation is the simulated moving-bed technique, for example, that described in U.S. Pat. No. 2,985,589 issued May 23, 1961 to D. B. Broughton et al. In this method of operation, the selection of a suitable displacing or desorbing agent or fluid (solvent) must take into account the requirements that it be capable of readily displacing adsorbed alcohol from the adsorbent bed and also that alcohol from the feed mixture be able to displace adsorbed desorbing agent from a previous desorption step. Further, the desorbing agent employed should be readily separable from admixture with the sugar alcohol components of the feedstock. Therefore it is contemplated that a desorbing agent having characteristics which allow it to be easily fractionated from the sugar alcohol should be used. For example, volatile desorbing agents should be used, such as alcohols, ketones, admixtures of alcohols and water, particularly methanol and ethanol. The most preferred desorbing agent is water.

While it is possible to utilize the activated adsorbent zeolite crystals in a non-agglomerated form, it is generally more feasible, particularly when the process involves the use of a fixed adsorption bed, to agglomerate the crystals into larger particles to decrease the pressure drop in the system. The particular agglomerating agent and the agglomeration procedure employed are not critical factors, but it is importat that the bonding agent be as inert toward the sugar alcohols and desorbing agent as possible. The proportions of zeolite and binder are advantageously in the range of 4 to 20 parts zeolite per part binder on an anhydrous weight basis.

The temperature at which the adsorption step of the process should be carried out should be from about 30° C. to the boiling point of the sugar alcohol solution (about 110° C.). It has been found that at temperatures below about 30° C. the counter-diffusion rate between sugar alcohols is too slow, i.e., a sufficient selectivity for the sorbitol or mannitol is not exhibited by the zeolite. As the temperature increases, the temperature at which the desorbent boils will be reached. Preferably, the adsorption step should take place between about 50° C. and about 90° C., most preferably between 60° and 80° C. Pressure conditions must be maintained so as to keep the system in liquid phase. High process temperatures needlessly necessitate high pressure apparatus and increase the cost of the process.

The preferable method for practicing the process of this invention is separation by chromatographic column. In this method, a sugar alcohol solution containing the mixture of sugar alcohols to be separated is injected for a short period of time at the top of the column and eluted down through the column with water. As the mixture passes through the column, chromatographic separation leads to a zone increasingly enriched in the adsorbed sugar alcohol. The degree of separation increases as the mixture passes further down through the column until a desired degree of separation is achieved. At this point, the effluent from the column is first shunted to one receiver which collects a pure product. Next, during the period of time when there is a mixture of sugar alcohols emerging from the column, the effluent is directed towards a "receiver for mixed product".

Next, when the zone of adsorbed alcohol emerges from the end of the column, the effluent is directed to a receiver for that product.

As soon as the chromatographic bands have passed far enough through the column, a new slug is introduced at the entrance of the column and the whole process cycle is repeated. The mixture which exits from the end of the column between the times of appearance of the pure fractions is recycled back to the feed and passed through the column again, to extinction.

The degree of separation of the two peaks as they pass through this chromatographic column will increase as the column length is increased. Therefore, one can design a column of sufficient length to provide any desired degree of separation of the two components from each other, even where the degree of overlap of the two peaks is the greatest.

Therefore, it is also possible to operate such a process in a mode which will involve essentially no recycle of an unseparated mixture back to the feed. However, if high purities are required such a high degree of separation may require an exceptionally long column. In addition, as the components are eluted through the column their average concentrations gradually decline. In the case of the sugar alcohols being eluted with water, this would mean that the product streams would be increasingly diluted with water. Therefore, it is highly likely that an optimum process (to achieve high degrees of purity of the two components) should involve the use of a much shorter column (than would be required for complete separation of the peaks) and also involve separating out the portion of the effluent containing the mixture of both peaks and recycling it to feed, as discussed above.

Another method for practicing the process of this invention is illustrated by the drawing in FIG. 5. In this method, a number of fixed beds are connected to one another by conduits which are also connected to a special valve. The valve subsequentially moves the liquid feed and product takeoff points to different positions around a circular array of the individual fixed beds in such a manner as to simulate countercurrent motion of the adsorbent. This process is well-suited to binary separations.

In the drawings, FIG. 5 represents a hypothetical moving-bed countercurrent flow diagram involved in carrying out a typical process embodiment of the present invention.

With reference to the drawing, it will be understood that whereas the liquid stream inlets and outlets are represented as being fixed, and the adsorbent mass is represented as moving with respect to the counter flow of feedstock and desorbing material, this representation is intended primarily to facilitate describing the functioning of the system. In practice the sorbent mass would ordinarily be in a fixed bed with the liquid stream inlets and outlets moving with respect thereto. Accordingly, a feedstock comprising a mixture of mannitol with sorbitol and/or galactitol is fed into the system through line 10 to adsorbent bed 12 which contains particles of regenerated zeolite BaX or BaY adsorbent in transit downwardly therethrough. The temperature is at 70° C. throughout the entire system and the pressure is substantially atmospheric. The component of the feedstock is adsorbed preferentially on the zeolite particles moving through bed 12, and the raffinate is entrained in the liquid stream of water desorbing agent leave bed 12 through line 14 and a major portion thereof is withdrawn through line 16 and fed into evaporation apparatus 18 wherein the mixture is fractionated and the concentrated raffinate is discharged through line 20. The water desorbing agent leaves the evaporation apparatus 18 through line 22 and if fed to line 24 through which it is admixed with additional desorbing agent leaving the adsorbent bed 26, and is recycled to the bottom of adsorbent bed 30. The zeolite BaX or BaY carrying adsorbed sugar alcohol passes downward through line into bed 30 where it is counter-currently contacted with recycled desorbing agent which effectively desorbs the sugar alcohol therefrom before the adsorbent passes through bed 30 and enters line 32 through which it is recycled to the top of adsorbent bed 26. The desorbing agent and desorbed sugar alcohol leave 30 through line 34. A portion of this liquid mixture is diverted through line 36, where it passes evaporation apparatus 38, and the remaining portion passes upward through adsorbent bed 12 for further treatment as hereinbefore described. In evaporation apparatus 38, the desorbing agent and sugar alcohol are fractionated. The sugar alcohol product is recovered through line 40 and the desorbing agent is either disposed of or passed through line 42 into line 24 for recycle as described above. The undiverted portion of the desorbing agent-/raffinate mixture passes from bed 12 through line 14 enters bed 26 and moves counter-currently upward therethrough with respect to the desorbing agent-laden zeolite adsorbent passing downwardly therethrough from recycle line 32. The desorbing agent passes from bed 26 in a relatively pure form through recycle line 24 and to bed 30 as hereinbefore described.

The following examples are illustrative of the practice of this invention. However, they do not limit the invention to the embodiments in the Examples.

As used in the Examples appearing below the following abbreviations and symbols have the indicated meaning:

KY: Potassium-exchanged zeolite Y
BaX: Barium-exchanged zeolite X
gpm/ft$^2$: gallons per minute per square foot

EXAMPLE 1

A 40-centimeter column having an inside diameter of 0.77 centimeters was loaded with KY powder zeolite. The column was filled with water and maintained at a temperature of 160° F. Water was then pumped through the column and a flow rate of 0.53 gpm/ft$^2$ was maintained. For a period of one minute a solution containing 2 weight percent galactitol and 2 weight percent mannitol ("feed pulse") was substituted for the water stream. After the one-minute feed pulse, the water feed which contained no dissolved sugar alcohols was reestablished. The composition of the effluent stream was monitored by a refractive index detector. The elution curve is given in FIG. 1. FIG. 1 shows that galactitol and mannitol are not separated using KY.

EXAMPLE 2

Figure 2:
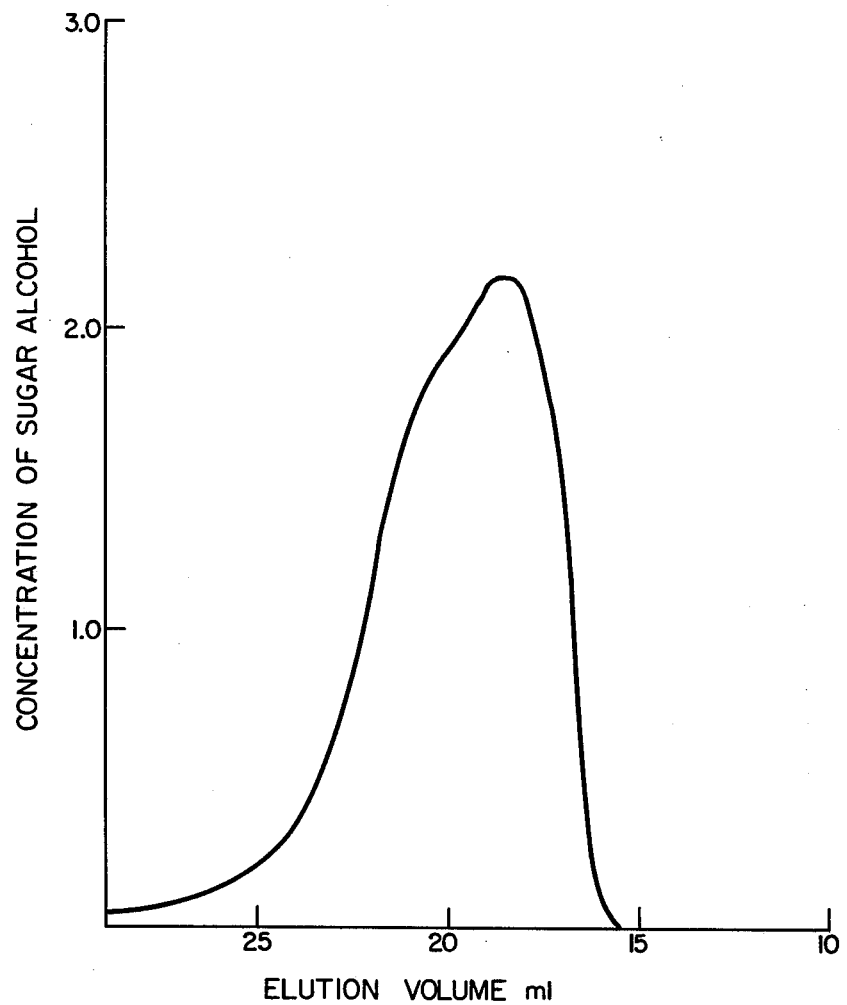

The same column and experimental procedures used in Example 1 were used. However, this compositon of the feed pulse solution was changed to 3% mannitol and 7% sorbitol. The elution curve is given in FIG. 2. This shows that mannitol and sorbitol are not separated using KY.

EXAMPLE 3

Figure 3:
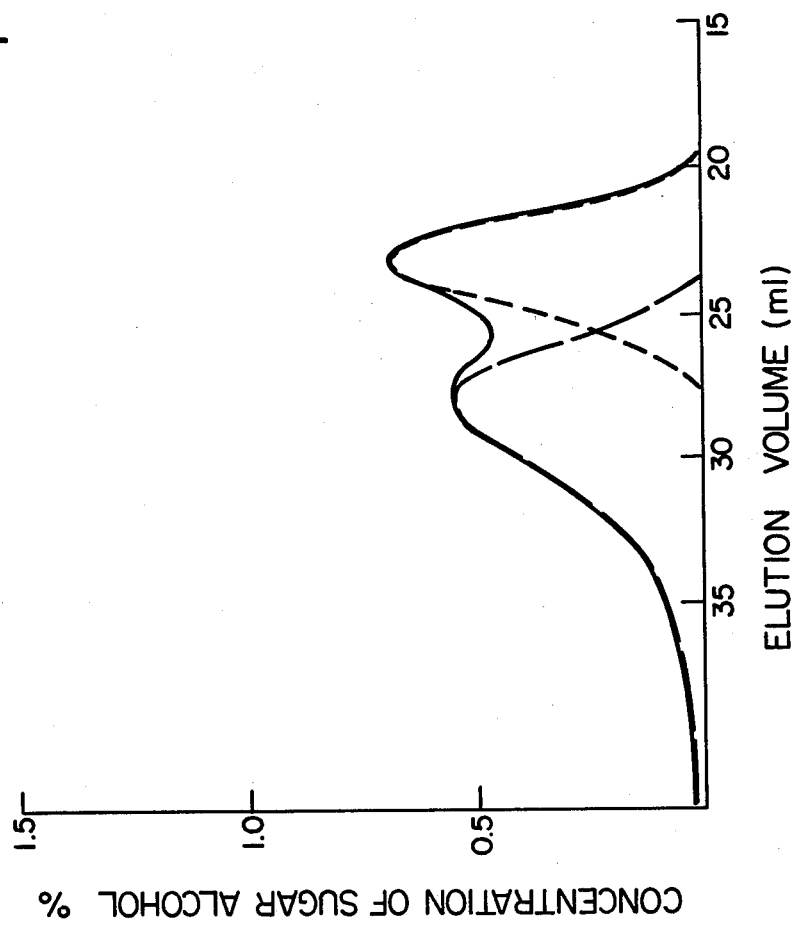
FIGS. 3 and 4 show elution curves of polyhydric alcohols where the separation medium is barium-substituted zeolite Type X.

The same experimental procedures used in Example 1 were employed. However, the zeolite was changed to BaX. The feed pulse was 2% galactitol and 2% mannitol. The elution curve is shown in FIG. 3. FIG. 3 shows that galactitol and mannitol are separated using BaX, galactitol being eluted first.

EXAMPLE 4

Figure 4:
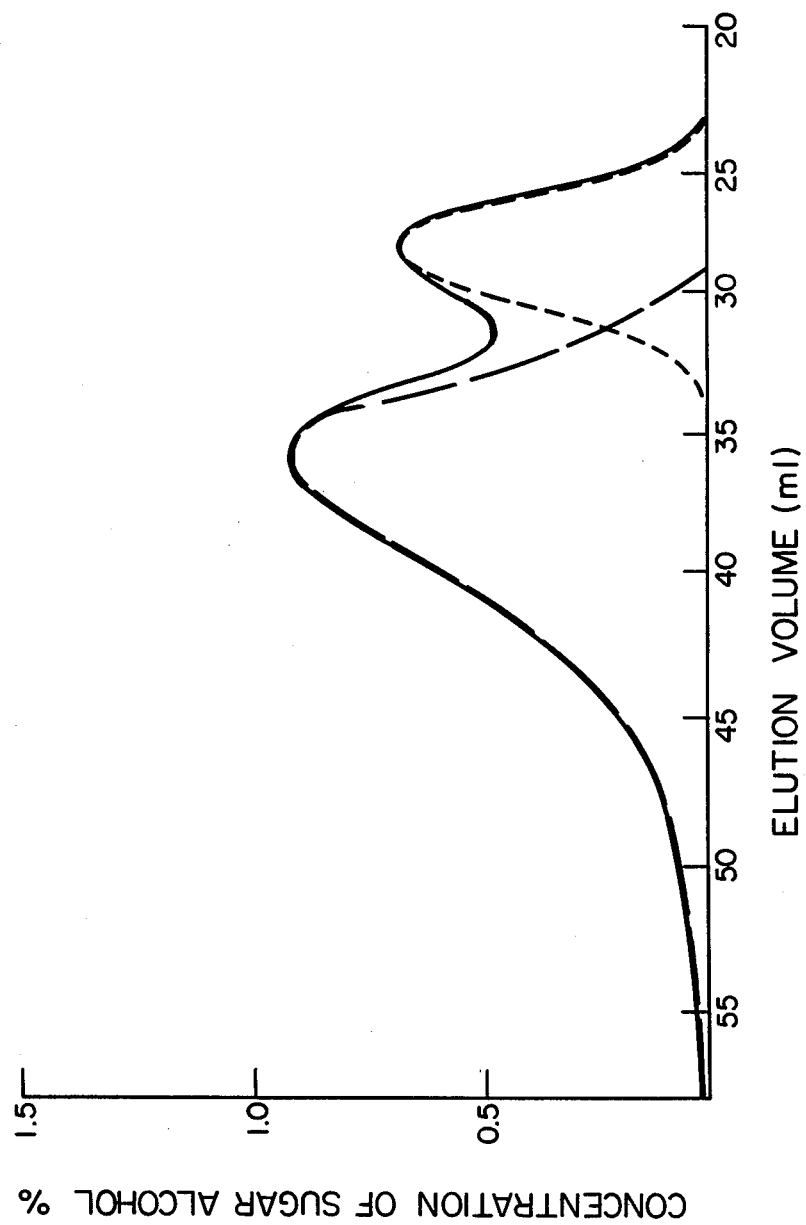

The same column and experimental procedures used in Example 3 were employed. However, the feed pulse solution was changed to one containing 3% mannitol and 7% sorbitol. FIG. 4, showing the elution curve, indicates that BaX separates mannitol from sorbitol.

What is claimed is:

1. A process for separating mannitol from galactitol by selective adsorption which comprises contacting a mixture comprising said compounds at a temperature of from about 30° C. to 110° C. and at a pressure sufficient to maintain the system in the fluid phase with an adsorbent composition comprising at least one crystalline aluminosilicate zeolite of type X in which the zeolitic cations which occupy more than 55% of the available cation sites are barium; whereby the mannitol is selectively adsorbed thereon, removing the non-adsorbed portion of said mixture from contact with the zeolite adsorbent, and desorbing the mannitol therefrom by contacting said adsorbent with a desorbing agent and recovering the desorbed mannitol.

2. A process for separating mannitol from galactitol by selective adsorption which comprises contacting a mixture comprising said compounds at a temperature of from about 30° C. to 110° C. and at a pressure sufficient to maintain the system in the fluid phase with an adsorbent composition comprising at least one crystalline aluminosilicate zeolite of type Y in which the zeolitic cations which occupy more than 55% of the available cation sites are barium; whereby the mannitol is selectively adsorbed thereon, removing the non-adsorbed portion of said mixture from contact with the zeolite adsorbent, and desorbing the mannitol therefrom by contacting said adsorbent with a desorbing agent and recovering the desorbed mannitol.

3. A process for separating sorbitol from mannitol by selective adsorption which comprises contacting a mixture comprising said compounds at a temperature of from about 30° C. to 110° C. and at a pressure sufficient to maintain the system in the fluid phase with an adsorbent composition comprising at least one crystalline aluminosilicate zeolite of type X in which the zeolitic cations which occupy more than 55% of the available cation sites are barium; whereby the sorbitol is selectively adsorbed thereon, removing the non-adsorbed portion of said mixture from contact with the zeolite adsorbent, and desorbing the sorbitol therefrom by contacting said adsorbent with a desorbing agent and recovering the desorbed sorbitol.

4. A process in accordance with claim 1 wherein the temperature is from about 50° C. to about 90° C.

5. A process in accordance with claim 4 wherein the temperature is from about 60° C. to about 80° C.

6. A process in accordance with claim 1 wherein the desorbent is selected from the group consisting of alcohols, ketones and water.

7. A process in accordance with claim 6 wherein the desorbent is water.

8. A process in accordance with claim 2 wherein the temperature is from about 50° C. to about 90° C.

9. A process in accordance with claim 8 wherein the temperature is from about 60° C. to about 80° C.

10. A process in accordance with claim 2 wherein the desorbent is selected from the group consisting of alcohols, ketones and water.

11. A process in accordance with claim 10 wherein the desorbent is water.

12. A process in accordance with claim 3 wherein the temperature is from about 50° C. to about 90° C.

13. A process in accordance with claim 12 wherein the temperature is from about 60° C. to about 80° C.

14. A process in accordance with claim 3 wherein the desorbent is selected from the group consisting of alcohols, ketones and water.

15. A process in accordance with claim 14 wherein the desorbent is water.

* * * * *